United States Patent [19]

Sugimoto et al.

[11] Patent Number: 5,759,572
[45] Date of Patent: Jun. 2, 1998

[54] LIPOSOME WITH OLIGOSACCHARIDE ON SURFACE

[75] Inventors: Masanobu Sugimoto; Kazue Ohishi, both of Saitama; Masakazu Hatanaka, Kyoto; Tsuguo Mizuochi, Tokyo, all of Japan

[73] Assignee: Tonen Corporation, Tokyo, Japan

[21] Appl. No.: 481,300

[22] PCT Filed: Oct. 28, 1994

[86] PCT No.: PCT/JP94/01828

§ 371 Date: Sep. 18, 1995

§ 102(e) Date: Sep. 18, 1995

[87] PCT Pub. No.: WO95/11704

PCT Pub. Date: May 4, 1995

[30] Foreign Application Priority Data

Oct. 29, 1993 [JP] Japan ................................ 5-272693

[51] Int. Cl.$^6$ ................................ A61K 9/127; A61K 45/00
[52] U.S. Cl. ................ 424/450; 424/278.1; 424/279.1
[58] Field of Search ................ 424/278.1, 279.1, 424/450

[56] References Cited

U.S. PATENT DOCUMENTS 5,169,636 12/1992 Nanba et al. .................. 424/450
5,686,103 11/1997 Redziniak et al. ............... 424/450

FOREIGN PATENT DOCUMENTS 60-45588 3/1985 Japan.
63-159402 7/1988 Japan.

*Primary Examiner*—Ponnathapura Achutamurthy
*Attorney, Agent, or Firm*—Michael N. Meller

[57] ABSTRACT

There are provided liposomes as an adjuvant which is effective for cellular immunity, has low toxicity and antigenicity, and may be administered to humans. The liposomes have oligosaccharide on their surface which consists of 2 to 11 saccharide residues and binds to lectin of antigen presenting cells. A vaccine may be prepared by reconstituting an antigen into the liposomes.

12 Claims, 4 Drawing Sheets

P; STATISTICAL SIGNIFICANCE WITH RESPECT TO I-1

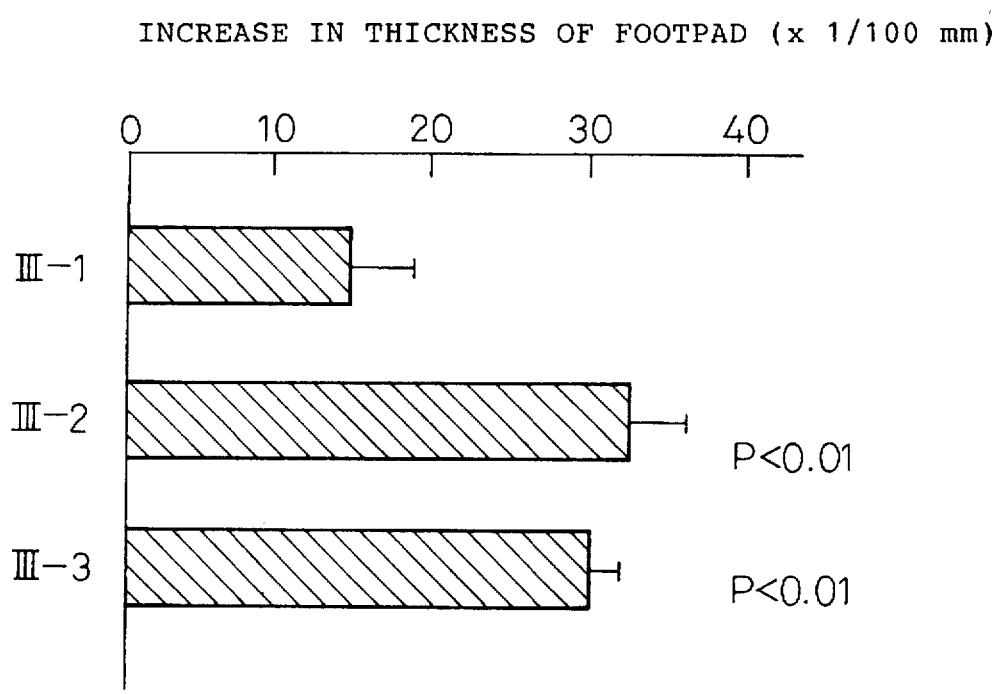

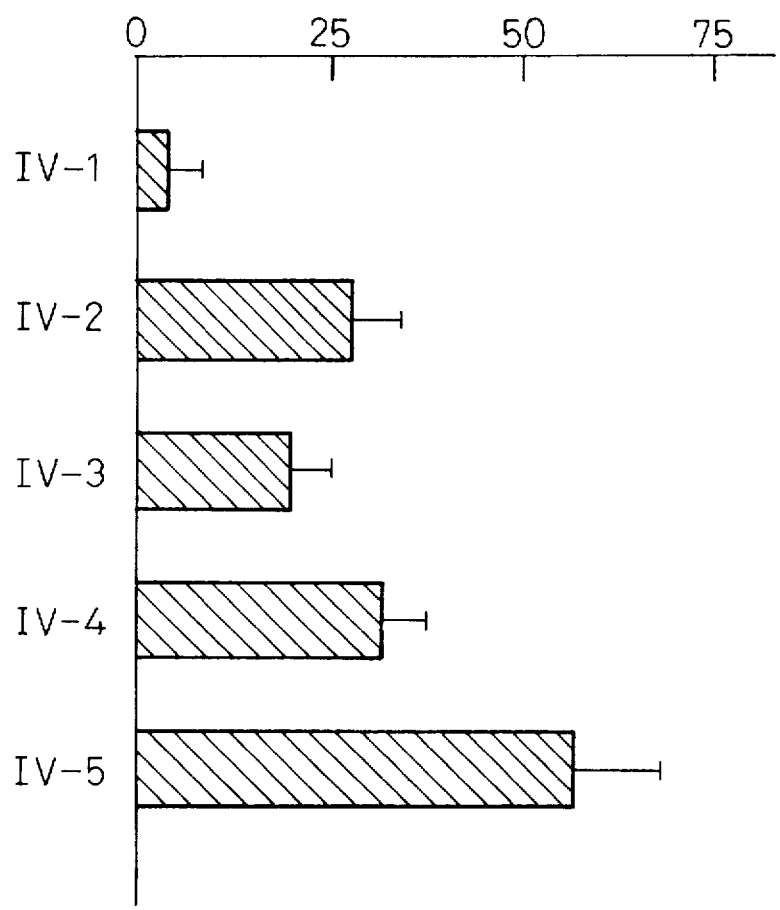

LIPOSOME WITH OLIGOSACCHARIDE ON SURFACE

TECHNICAL FIELD

The present invention relates to a method of producing a liposome preparation capable of efficiently inducing cellular immunity, and the liposome may be widely used as an adjuvant (immunostimulating aid) for vaccines and immunotherapeutic agents.

BACKGROUND ART

Because antigens in vaccines and immunotherapeutic agents generally do not elicit an effective immune response by themselves, adjuvants are used as aids to increase immunogenicity. Many substances and preparations with an adjuvant action have been reported as a result of research, but most of these have not been put into practical use due to their strong toxicity, except for aluminum phosphate adjuvants and alum adjuvants, consisting mainly of aluminum hydroxide, being suitable for use in humans.

As an alternative method, there is described in Japanese Unexamined Patent Publication No. 2-188532 a liposome vaccine prepared by reconstructing an antigen-presenting glycoprotein into a liposome. Immunity is largely classified into humoral immunity and cellular immunity, and although alum adjuvants are capable of inducing humoral immunity in a relatively efficient manner, they are not very effective at inducing cellular immunity. Yet in recent years it has gradually become clear that the role of cellular immunity is very important in treatment of persistently infectious viral diseases such as AIDS (J. Salk et al., Science 260, 1270–1271, 1993; M. Sugimoto, K. Ohishi and Y. Ikawa, Immunol. Today 14, 190–191, 1993).

Consequently, there has emerged a need to develop adjuvants capable of inducing strong cellular immunity. Liposomes coated with high-molecular polysaccharides such as mannan are reported to have strong cellular immunity-inducing properties (Y. Noguchi et al., J. Immunol., 143, 3737–3742, 1989). Also, WO92/04887 describes liposomes coated with mannose-containing polysaccharides. However, mannan is a mixture of polymannoses of differing sizes, and it is known to exhibit a strong toxicity in the body (Mikami, K. et al., Summary of 15th Carbohydrate Symposium, 43–44, 7/29/93, 30 days, Sendai), and is thus not suitable for use as a drug.

In other words, mannan, being a large polysaccharide consisting of 50 to 100 mannose residues, is also non-uniform in terms of molecular weight, and little is known about its structure, including saccharide bond forms. This polysaccharide produces antibodies when inoculated into animals (it has antigenicity), and as mentioned above it is known to be highly toxic.

DISCLOSURE OF THE INVENTION

The present invention, therefore, is aimed at providing a liposome to be used for humans, which has effective adjuvant activity to induce cellular immunity and which has low toxicity and antigenicity.

As a result of much research intended to overcome the above-mentioned problems, the present inventors have found that liposomes which have oligosaccharide on their surface which consists of 2 to 11 saccharide residues and binds to lectin of antigen presenting cells has effective adjuvant activity to induce cellular immunity and also has low toxicity and antigenicity, to allow its use for humans.

Consequently, the present invention provides liposomes which have oligosaccharide on their surface which consists of 2 to 11 saccharide residues and binds to lectin of antigen-presenting cells.

The present invention further provides a vaccine prepared by encapsulating an antigen in the above-mentioned liposomes.

BRIEF DESCRIPTION OF THE DRAWINGS

FIG. 3 is a graph showing the results of Experiment III.

FIG. 4 is a graph showing the results of Experiment IV.

Figure 1:
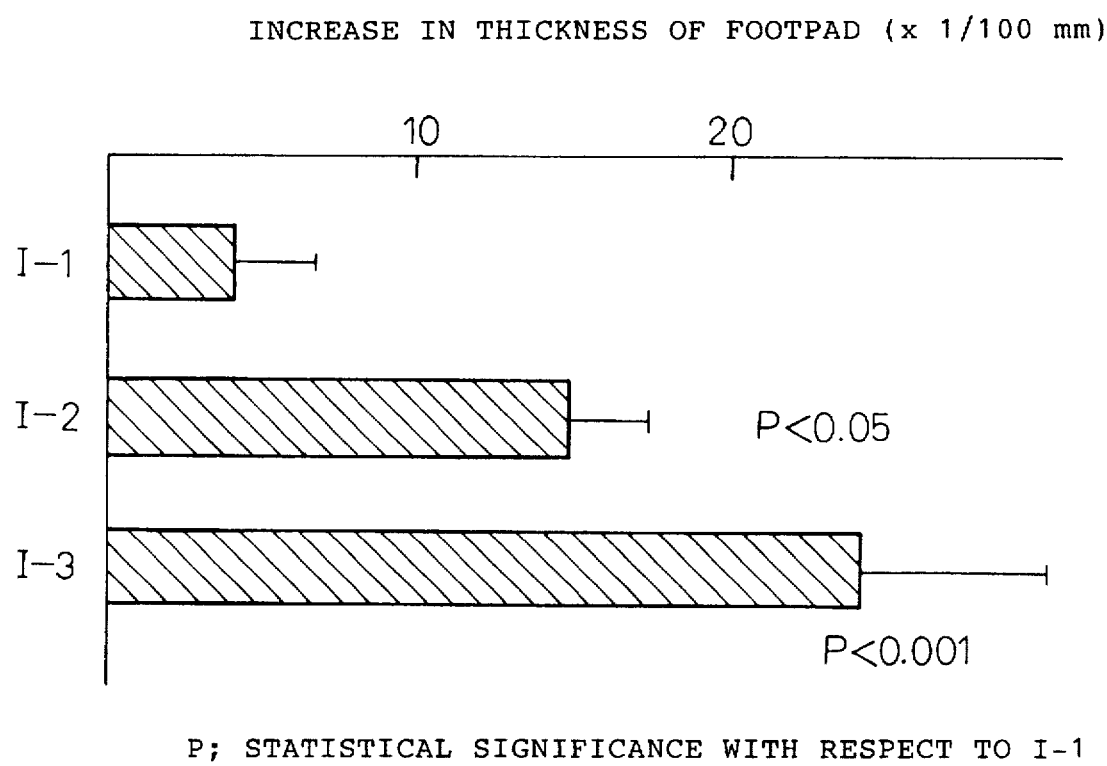
FIG. 1 is a graph showing the results of Experiment I.

In the figures, the shaded bars indicate average arithmetic means, and the solid lines indicate standard error.

DETAILED DESCRIPTION OF THE INVENTION

The liposomes of the present invention have effective adjuvant activity to induce cellular immunity while both their toxicity and own antigenicity are considered to be low; consequently they may be used as an antigen adjuvant for vaccines and are likely to be administered to humans. Particularly strong vaccines may be obtained by reconstituting an objective antigen or immunogen into such liposomes.

The liposome of the present invention has on its surface an oligosaccharide capable of binding to lectin of antigen-presenting cells, and which has 2 to 11 saccharide residues. Here, the term "antigen-presenting cells" refers to macrophages, dendritic cells, and the like. Furthermore, the lectin of antigen-presenting cells refers to mannose receptors which are present on the surface of antigen-presenting cells.

The monosaccharides making up the oligosaccharide are themselves preferred to have the property of binding to lectin of antigen-presenting cells, and examples of saccharides recognized by macrophage mannose receptors, in the order of recognition strength, are D-mannose (D-Man), L-fucose (L-Fuc)>D-N-acetylglucosamine (D-GlcNAc), D-glucose (D-Glc)>D-galactose (D-Gal), D-N-acetylgalactosamine (D-GalNAc) and D-rhamnose (D-Rha) (B. L. Largent et al., J. Biol. Chem. 259, 1764–1769, 1984). However, it is enough if the oligosaccharide itself binds to lectin of antigen presenting cells, and it may also include structural saccharides which do not bind to lectin of antigen presenting cells.

The structural saccharides in the oligosaccharide are linked with an α1→2 bond, α1→3 bond, α1→4 bond, α1→6 bond or β1→4 bond or a combination of these bonds. For example, mannose may form a simple chain with the above-mentioned bonds, or it may take a branched structure with a combination of α1→3 and α1→6 bonds. The number of monosaccharides in the oligosaccharide is preferably 2 to 11. Specific oligosaccharides which may be mentioned include, for example, mannobiose (Man2), mannotriose (Man3), mannotetraose (Man4), mannopentaose (Man5), mannohexaose (Man6), mannoheptaose (Man7) and various mixed oligosaccharides such as M5 (compound 1) and RN (compound 2) shown below.

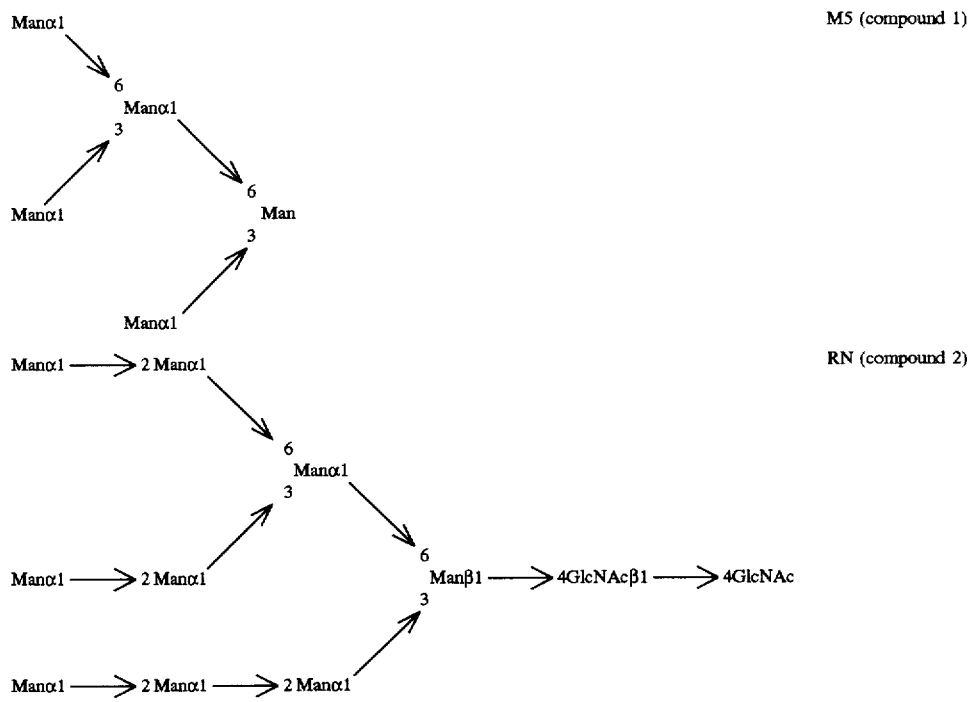

M5 (compound 1)

RN (compound 2)

wherein one or both of Man monomers bonded with α1→2 bond may be present or absent independently.

In addition, glucose-containing oligosaccharides include those having the structure indicated by compound 3, N-acetylglucosamine-containing oligosaccharides include those having the structure indicated by compound 4, and fucose-containing oligosaccharides include those having the structure indicated by compound 5.

wherein p is 0 or 1 and each n is independently 0 to 3. One or both of the two GlcNAc residues shown as 4GlcNAcβ1→4GlcNAc at the right of the formula may either be present or absent independently. Also, any of the GlcNAc residues shown as $(GlcNAc\beta 1\rightarrow)_n$, may be glycoside-linked to any free hydroxyl group of the Man residue present the right side of the GlcNAc.

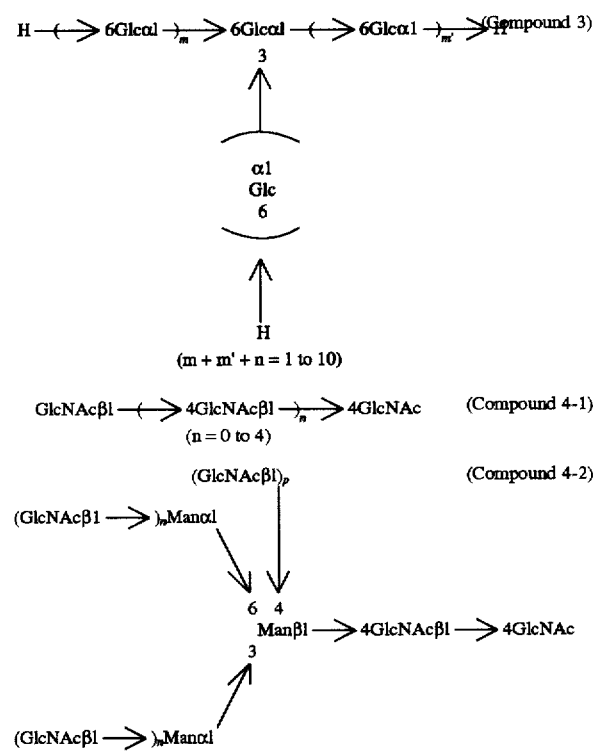

(Compound 3)

(m + m' + n = 1 to 10)

(Compound 4-1) (n = 0 to 4)

(Compound 4-2)

(Compound 4-3)

wherein p is 0 or 1 and each n is independently 0 to 3. Also, any of the GlcNAc residues shown as $(GlcNAc\beta 1\rightarrow)_n$ may be glycoside-linked to any open hydroxyl group of the Man residue present the right side of the GluNAc.

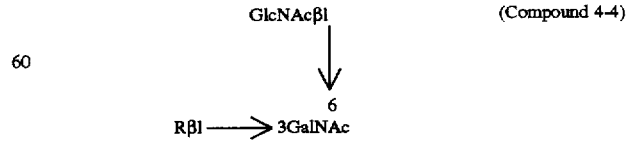

(Compound 4-4)

wherein R is H, GlcNAc or $(GlcNAc\beta 1\rightarrow 6)_p$ $(GlcNAc\beta 1\rightarrow 3)_p Gal$, wherein p is 0 or 1.

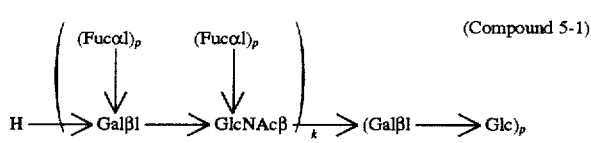

(Compound 5-1)

wherein k is 1 to 5 and each p is independently 0 or 1. Those without numbers at the ends of the arrows may be glycoside-linked to any free hydroxyl group.

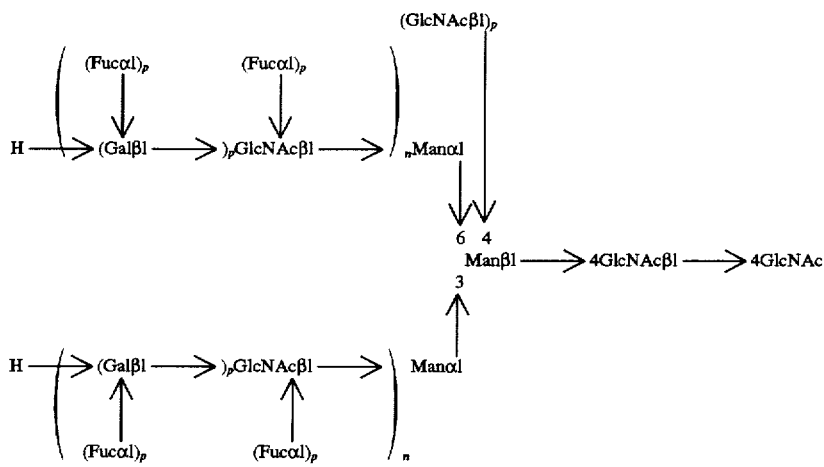

(Compound 5-2)

wherein each p is independently 0 or 1 and each n is independently 0 to 3. Those saccharides without numbers at the ends of the arrows may be glycoside-linked to any free hydroxyl group. Also, one or both of the two GlcNAc residues shown as 4GlcNAcβ1→4GlcNAc at the right of the formula may be present or absent independently.

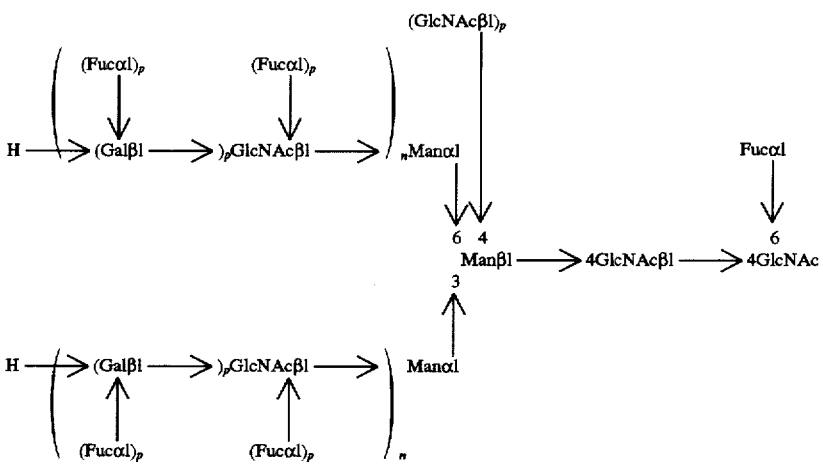

(Compound 5-3)

where each p is independently 0 or 1 and each n is independently 0 to 3. Those without numbers at the ends of the arrows may be glycoside-linked to any free hydroxyl group. Also, one or both of the two GlcNAc residues shown as 4GlcNAcβ1→4GlcNAc at the right of the formula may be present or absent independently.

All of the above-mentioned oligosaccharides have one reducing terminal aldehyde group. Therefore, the aldehyde group may be used as the means for introducing the oligosaccharide on the surface of the liposome. That is, a Schiff base may formed between this aldehyde and the amino group-containing lipid, and the oligosaccharide and the lipid may then be linked by reduction of the Schiff base, preferably chemical reduction such as reduction with $N_aBH_3CN$, using a common method (Mizuochi Tsuguo, Carbohydrate Engineering, pp.224–232, Industrial Board of Investigation Biotechnology Information Center, 1992).

The above-mentioned amino group-containing lipid is preferably an amino group-containing phospholipid, and for example there may be used a phosphatidylethanolamine such as dipalmitoyl phosphatidylethanolamine (DPPE), distearoyl phosphatidylethanolamine (DSPE), or the like.

According to the present invention, the oligosaccharide/lipid linked product obtained in the manner described above will sometimes be referred to as an "artificial glycolipid".

Lipids composing the liposome may be any conventional lipids known to be suitable for composing liposomes, used singly or in combination. For example, natural lipids obtained from egg yolk, soybean or other animals or vegetables, or such lipids which have been modified by lowering the degree of unsaturation by hydrogen addition, or chemically synthesized products, may be used. Specific examples include sterols such as cholesterol (Chol); phosphatidylethanolamines such as dipalmitoyl phosphatidylethanolamine (DPPE) and distearoyl phosphatidylethanolamine (DSPE); phosphatidylcholines such as dipalmitoyl phosphatidylcholine (DPPC) and distearoyl phosphatidylcholine (DSPC); phosphatidylserines such as dipalmitoyl phosphatidylserine (DPPS) and distearoyl phosphatidylserine (DSPS); phosphatidic acids such as dipalmitoyl phosphatidic acid (DPPA) and distearoyl phosphatidic acid; etc.

The liposomes are prepared using a per se known method (D. W. Deeamer, P. S. Uster, "Liposome" ed. by M. J. Ostro, Marcel Dekker Inc., N.Y. Basel, 1983, p.27). The vortex method and ultrasonic method are known, but other methods which may be applied include the ethanol infusion method, the ether method and the reverse phase evaporation method, used singly or in combination.

For example, when applying the vortex method or the ultrasonic method, lipid is dissolved in organic solvent such as methanol, ethanol, chloroform or a mixture thereof such as a mixture of methanol and chloroform, after which the organic solvent is evaporated off to obtain a thin lipid layer.

Next, an aliquote of aqueous medium is added to the thin lipid layer and it is subjected to vortex treatment or ultrasonic treatment to form liposomes. A desired antigen or immunogen which is to be the active component of vaccine is combined with the above-mentioned aqueous medium at this time, and for example, it may be dissolved or suspended to encapsulate the antigen or immunogen in the liposome.

Any of, for example, the following two methods may be used to introduce the oligosaccharide onto the surface of the liposome. In cases where the above-mentioned artificial glycolipid is water-soluble and does not dissolve sufficiently in organic solvents, for example when products of linking the above-mentioned M5 and DPPE (M5-DPPE), or RN and DPPE (RN-DPPE) are used, an aqueous solution may be prepared and mixed with the formed liposomes and incubated at, for example, 4° C. to room temperature for 24 to 120 hours, for example about 72 hours.

On the other hand, if the artificial glycolipid dissolves in inorganic solvents, the artificial glycolipid may be dissolved in the organic solvent together with the liposome-composing lipid, as described above for the liposome-producing process, and the liposome may then be formed by a conventional method.

The amount of the oligosaccharide with respect to the amount of liposomes will differ depending on the type of the oligosaccharide, the type of antigen to be reconstituted, the combination structure of the liposome, and so on, but in general it is between 5 µg and 500 µg per 1 mg of the lipid composing the liposome.

The liposomes of the present invention may be either of multilayer type (multilamella vesicles) or monolayer type (unilamella vesicles). These may be prepared by common known methods, and either type may be converted into the other type by a conventional method; for example, multilayer-type of liposomes may be converted into monolayer-type of liposomes. The particle size of the liposomes of the present invention is not particularly limited, and if necessary the particle size may be adjusted by a conventional method, such as by filtration through a filter of a given pore size.

The antigen to be reconstituted into the liposomes of the present invention may be any water-soluble antigen. As such antigens the followings may be used for example; protein and peptide antigens, and particularly synthetic protein and peptide antigens, for example proteins, glycoproteins, peptides and glycopeptides prepared by extraction from a separation source, gene recombination or chemical synthesis. Examples of such antigens include coat proteins and core proteins, or partial peptides therefrom, of human immunodeficiency virus (HIV), influenza virus, malaria parasites, tubercule bacilli, and the like.

The proportion of the antigen to the liposome is extremely important, and will differ depending on the type of antigen, the composition and structure of the liposome, etc., but generally it is between 1 µg and 100 µg per 1 mg of the lipid composing liposomes.

Linkage of the oligosaccharide to the surface is proven by adding a lectin corresponding to the saccharide, and investigating the agglutination reaction of the liposome.

Liposomes reconstituted with a model antigen is usable to evaluate the effect of the saccharide, and the antigen is preferably a standard protein with high antigenicity which has been thoroughly documented, such as ovalbumin (OVA). The index of cellular immunity may be a delayed-type hypersensitivity (DTH) response in mice (with $T_H1$ cells).

As shown in the experiment described below, the objective adjuvant was capable of inducing a DTH response. Consequently, it may be used as an adjuvant for protective vaccines of causative agents in which $T_H1$ cells play a role, and for immunotherapeutic agents and cancer immunotherapeutic agents.

EXAMPLES

The present invention will now be explained in more detail by way of the following examples and experiments.

Example 1
Preparation of artificial glycolipid

To 2.5 to 5 mg each of $\alpha 1 \rightarrow 3$ linked mannobiose (Man2), mannotriose (Man3) having the structure Man$\alpha 1 \rightarrow 6$ (Man$\alpha 1 \rightarrow 3$)Man, M5 (compound 1) and RN (compound 2), 600 µl of distilled water was added, and each mixture was stirred to dissolution to prepare an oligosaccharide solution.

On the other hand, DPPE was dissolved in a mixture of chloroform/methanol (1:1 volume ratio) to a concentration of 5 mg/ml to prepare a DPPE solution. Also, $N_aBH_3CN$ was dissolved in methanol to a concentration of 10 mg/ml to prepare a $N_a$BH3CN solution.

To 600 µl of the above-mentioned oligosaccharide solution, 9.4 ml of the DPPE solution and 1 ml of the $N_aBH_3CN$ solution were added, and the mixture was stirred. This reaction mixture was incubated at 60° C. for 16 hours to produce an artificial glycolipid. The reaction solution was purified with a silica gel column and a C18 reverse phase column to obtain the purified artificial glycolipid. A commercially available mannan cholesterol product (Dojin Chemical) was also used.

Example 2
Preparation of antigen-encapsulating liposome

A 10-mM DPPC-containing chloroform/methanol (2:1, V/V) solution (hereunder referred to as C/M solution) and a 10-mM cholesterol (Chol)-containing C/M solution were mixed at a proportion of 2:1 (usually, total: 3 ml) and the mixture was added to a 25 ml pear-shaped flask which was connected to an evaporator, and the C/M solution was evaporated off at 40° C. under reduced pressure. At this time, in the cases where the oligosaccharide to be added to coat the surface of the liposome was mannobiose (Man2) or mannotriose (Man3), the artificial glycolipids prepared therefrom and the DPPE for comparison were dissolved in chloroform and added at a ⅟₁₀ molar ratio with respect to the DPPC.

A thin lipid layer was formed at the bottom of the flask, chloroform was added thereto to dissolve the layer, and then the solvent was again evaporated off. This procedure was repeated 2 to 3 times to result in the formation of a smooth thin lipid layer. The flask was placed in a desiccator for at least one hour to completely remove the solvent, and then distilled water was added and the mixture was subjected to a vortex for hydration. The content was transferred to a test tube and pre-cooled at −80° C. for 20 minutes until frozen, and then subjected to a lyophilization to remove the water.

An aqueous solution containing ovalbumin (OVA) (normally 10 mg/ml) as the model antigen was added, and the mixture was subjected to vortex for hydration, and OVA-reconstituted liposomes were formed. PBS (phosphate-buffered saline) was added to the liposome suspension and centrifuged at 15,000 rpm, and the supernatant was removed. After this procedure was repeated, the precipitate was used as liposomes. This was multilamella vesicle-(multilayer-) type liposomes.

In the cases where the oligosaccharide to coat the surface of liposomes was M5 or RN, or mannan (Mn) (comparison), the artificial glycolipid prepared therefrom was dissolved in PBS to a concentration of 2–10 mg/ml, this solution was combined with the liposome prepared above at a volume ratio of 5:1, and the mixture was incubated at room temperature for 3 days to adsorb the oligosaccharide onto the surface of liposomes. By measuring the unadsorbed saccharide it is possible to determine the amount of coated glycolipid. All of liposomes were modified with glycolipids, but for simplicity the glycolipids are referred to only in terms of the saccharides, "M5" or "mannan".

The amounts of OVA, Chol and each saccharide contained in the completed liposomes were assayed in the following manner. For OVA, the liposome was dissolved in the surfactant sodium dodecyl sulfate, and the solution was subjected to separation by SDS-PAGE electrophoresis and dyeing with Coomassie brilliant blue (CBB). The degree of dyeing was quantified by densitometry, and the amount of protein was calculated by comparison with a standard sample of OVA. For Chol, the assay was made using a clinical diagnosis kit (Wako Junyaku Kogyo, K.K.), by the cholesterol oxidase/p-chlorophenol method. The saccharide content was assayed by the anthrone- sulfuric acid method.

By following the above procedures, liposomes containing OVA, Chol and glycolipid (dosage per mouse) as listed in Table 1 were prepared.

TABLE 1

| Experiment | Liposome | OVA (µg) | Chol (µg) | Glycolipid (µg) |
|---|---|---|---|---|
| I | 1 | 5.0 | 80.2 | 0 |
|  | 2 | 5.0 | 80.2 | 166.7 (M5) |
|  | 3 | 5.0 | 80.2 | 237.5 (Mn) |
| II | 1 | 12.3 | 70 | 0 |
|  | 2 | 12.3 | 70 | 185.8 (M5) |
|  | 3 | 12.3 | 70 | 3.1 (RN) |
|  | 4 | 12.3 | 70 | 68.0 (Mn) |
| III | 1 | 6.0 | 60 | DPPE |
|  | 2 | 5.5 | 60 | Man2-DPPE |
|  | 3 | 10.3 | 60 | Man3-DPPE |

Notes:
(1) Values (µg) are amounts per mouse
(2) The amounts of glycolipid in Experiment III are a 1/10 molar ratio with respect to DPPC.

Notes: (1) Values (µg) are amounts per mouse (2) The amounts of glycolipid in
Experiment III are a 1/10 molar ratio with respect to DPPC.
Experiments: Induction of a delayed-type hypersensitivity (DTH) response in mice The above liposomes were inoculated to Balb/c mice (female, 6 weeks old), each group consisting of 5 mice, and the cellular immunity-inducing ability was evaluated by a DTH footpad swelling response. Each of the liposomes listed above were suspended in 0.2 ml PBS, and 0.1 ml thereof was subcutaneously inoculated at each of two places on the dorsal side of mice. At one week after inoculation, 40 µg OVA/22 µg alum/25 µl PBS was injected into the left footpad, and 22 µg alum/25 µl PBS into the right footpad as a control, and at 24 hours thereafter, the thickness of the left and right footpads was measured. The difference between the thickness of the right and left footpads was used as the index for a specific DTH response.

The results of Experiment I are shown in FIG. 1. The liposomes coated with M5 induced a statistically significantly stronger DTH response than the non-coated ones. Mn had a similar augmenting effect, the degree of which was about the same as M5. That is, there was no statistically significant difference between M5 and Mn groups.

Figure 2:
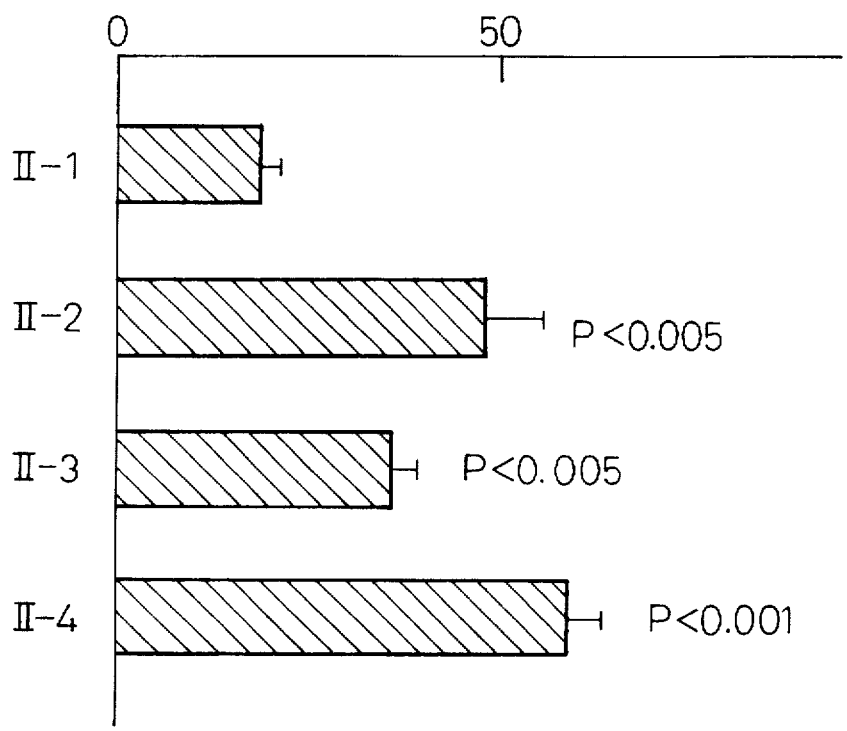
FIG. 2 is a graph showing the results of Experiment II.

The results of Experiment II are shown in FIG. 2. As expected, the liposomes coated with M5 or Mn induced a statistically significantly stronger DTH response than those not coated with saccharide. RN also had an enhancing effect on the DTH reaction which, though weak, was statistically significant. However, there was no significant difference between M5 and Mn.

To summarize the above two experiments, it is clear that M5 and Mn have roughly equal effects in terms of the induction of a DTH response when they were applied to liposomes.

The results of Experiment III are shown in FIG. 3. Adjuvant activity was compared among OVA-reconstituted liposomes containing DPPE (control) and those containing, instead of DPPE, a conjugate of oligosaccharide and DPPE. Of these, only the groups of mannobiose (Man2) and mannotriose (Man3) induced a statistically significantly stronger DTH response as compared with the control.

No significant activity was found for conjugates of DPPE with mannose, lactose or galactose (data not shown).

From the results described above it is clear that the conjugates of DPPE with oligosaccharide such as oligomannose consisting of at least 2 to 11 saccharide residues have an effect to augment a DTH response-inducing ability of liposomes when the conjugates were added to the liposomes or applied onto the liposomes. Also, since mannan has a similar effect, oligomannoses with longer length may have the same effect.

The results of Experiment IV are shown in FIG. 4. For comparison the effect of conventional alum adjuvant used as a control is shown. Mice were inoculated with the followings: OVA; mannan-coated liposomes without OVA (IV-1) as a control, OVA in saline (IV-2), OVA in conventional alum adjuvant (IV-3), OVA reconstituted into non-coated liposomes (IV-4) or OVA reconstituted into mannan-coated liposomes (IV-5). The doses per mouse were; 12.5 µg for OVA, 15 µg for alum and 40 µg for liposomes in terms of the amount of cholesterol.

In this experiment, no difference was found among the groups inoculated with OVA in saline, with alum adjuvant or reconstituted into non-coated liposomes. Rather, the alum adjuvant-inoculated group showed a tendency to have the lowest DTH-inducing ability among the three groups. Furthermore, the group inoculated with mannan-coated liposomes exhibited the highest immunogenicity. The DTH response of this group was statistically significantly stronger ($p<0.05$) than that of the alum adjuvant group.

From the results of FIGS. 1 to 4, it is concluded that liposomes coated with oligosaccharides such as mannan or oligomannose are superior to alum adjuvants in regard to the ability to induce a DTH response.

INDUSTRIAL APPLICABILITY

The liposomes of the present invention possess adjuvant activity to induce cellular immunity, with low toxicity and weak or no antigenicity, and may therefore be used as an antigen adjuvant for human vaccines. Particularly powerful vaccines may be obtained by reconstituting an objective antigen or immunogen into the liposomes.

We claim:

1. A liposome having an oligosaccharide on its surface wherein said oligosaccharide comprises mannose and is selected from the group consisting of mannobiose (Man2), mannotriose (Man3), mannotetraose (Man4), mannopentaose (Man5), mannohexaose (Man6) and mannoheptaose (Man7), and wherein said liposome is composed of one or more lipids selected from the group consisting of cholesterol (Chol); a phosphatidyletianolamine; a phosphatidylcholine; a phoshatidylserine; and a phosphatidic acid.

2. A liposome having an oligosaccharide on its surface wherein said oligosaccharide is an oligosaccharide represented by the following formula ME or RN below:

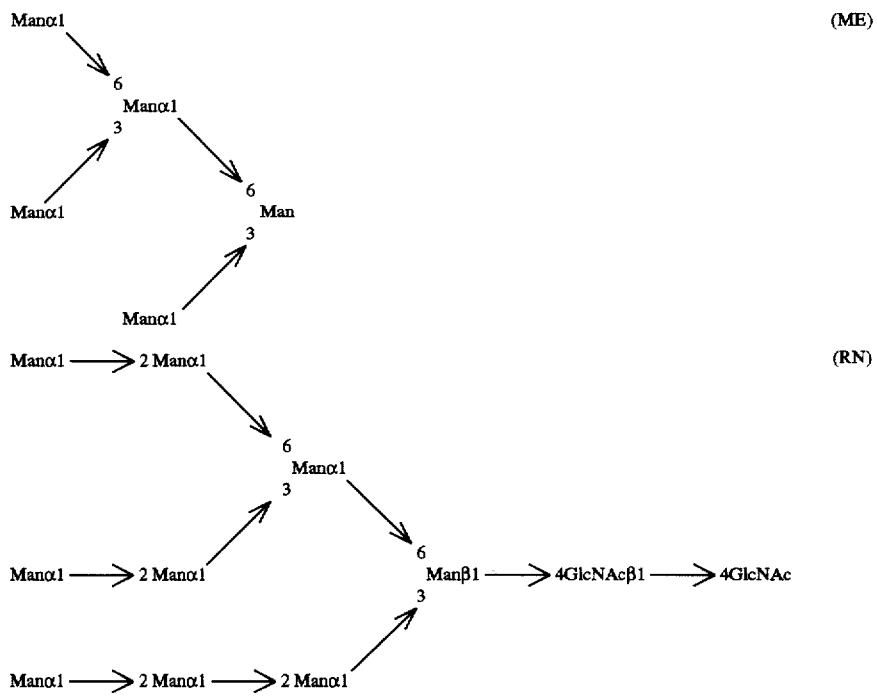

wherein one or both of Man monomers bonded with α1→2 bond may be present or absent independently, and wherein said liposome is composed of one or more lipids selected from the group consisting of cholesterol (Chol); a phosphatidylethanolamine; a phoghatidylcboline; a phosnhatidylserine and a phosphatidic acid.

3. A liposome according to claim 1, wherein the lipid which forms said liposome is a phosphatidylethanolamine, and the liposome and oligosaccharide are linked by reaction between the amino group of the lipid and the aldehyde of said oligosaccharide.

4. A liposome according to claim 2, wherein the lipid which forms said liposome is a phosphatidylethanolamine, and the liposome and oligosaccharide are linked by reaction between the amino group of the lipid and the aldehyde of said oligosaccharide.

5. A liposome according to claim 1, wherein the phosphatidylethanolamine is dipalmitoyl phosphatidylethanolamine (DPPE) or distearoyl phosphatidylethanolamine (DSPE), the phosphatidylcholine is dipalmitoyl phosphatidylcholine (DPPC) or distearoyl phosphatidylcholine (DSPC), the phosphatidylserine is dipalmitoyl phosphatidylserine (DSPS), and the phosphatidic acid is dipalmitoyl phosphatidic acid (DPPA) or destearoyl phosphatidic acid.

6. A liposome according to claim 2, wherein the phosphatidylethanolamine is dipalmitoyl phosphatidylethanolamine (DPPE) or distearoyl phosphatidylethanolamine (DSPE), the phosphatidlylcholine is dipalmitoyl phosphatidylcholine (DPPC) or distearoyl phosphatidylcholine (DSPC), the phosphatidylserine is dipalmitoyl phosphatidylserine (DSPS), and the phosphatidic acid is dipalmitoyl phosphatidic acid (DPPA) or destearoyl phosphatidic acid.

7. A liposome according to claim 3, wherein the phosphatidylethanolamine is dipalmiitoyl phosphatidylethanolamine (DPPE) or distearoyl phosphatidylethanolamine (DSPE).

8. A liposome according to claim 4, wherein the phosphatidylethanolamine is dipalmitoyl phosphatidylethanolamine (DPPE) or distearoyl phosphatidylethanolamine (DSPE) the phosphatidylcholine is dipalmitoyl phosphatidylcholine (DPPC) or distearoyl phosphatidylcholine (DSPC), the phosphatidylserine is dipalmitoyl phosphatidylserine (DSPS), and the phosphatidic acid is dipalmitoyl phosphatidic acid (DPPA) or destearoyl phosphatidic acid.

9. An immunogenic composition prepared by reconstituting an antigen into liposomes as defined in claim 1.

10. An immunogenic composition prepared by reconstituting an antigen into liposomes as defined in claim 2.

11. An immunogenic composition prepared by reconstituting an antigen into liposomes as defined in claim 3.

12. An immunogenic composition prepared by reconstituting an antigen into liposomes as defined in claim 4.

* * * * *